United States Patent
Ingalhalikar et al.

(10) Patent No.: US 10,595,902 B2
(45) Date of Patent: Mar. 24, 2020

(54) SELF-ACTUATING GROWING ROD SYSTEMS

(71) Applicant: Indius Medical Technologies Private Limited, Pune, Maharashtra (IN)

(72) Inventors: Aditya Vikas Ingalhalikar, Maharashtra (IN); Sagar Sanjeev Sathaye, Maharashtra (IN); Manali Suhas Kunte, Maharashtra (IN); Piyali Sanjeev Gokhale, Maharashtra (IN); Nikhil Vijay Butala, Maharashtra (IN)

(73) Assignee: INDIUS MEDICAL TECHNOLOGIES PRIVATE LIMITED, Pune (IN)

( * ) Notice: Subject to any disclaimer, the term of this patent is extended or adjusted under 35 U.S.C. 154(b) by 0 days.

(21) Appl. No.: 15/791,234

(22) Filed: Oct. 23, 2017

(65) Prior Publication Data

US 2018/0110543 A1 Apr. 26, 2018

(30) Foreign Application Priority Data

Oct. 24, 2016 (IN) .............................. 201621036216
Oct. 24, 2016 (IN) .............................. 201621036220

(51) Int. Cl.
*A61B 17/70* (2006.01)
*A61B 17/68* (2006.01)

(52) U.S. Cl.
CPC ...... *A61B 17/7017* (2013.01); *A61B 17/7004* (2013.01); *A61B 17/7025* (2013.01); *A61B 17/7028* (2013.01); *A61B 2017/681* (2013.01)

(58) Field of Classification Search
CPC ........................................... A61B 17/70–7046
See application file for complete search history.

(56) References Cited

U.S. PATENT DOCUMENTS

| | | | |
|---|---|---|---|
| 6,106,525 A * | 8/2000 | Sachse .............. | A61B 17/8004 606/59 |
| 8,585,740 B1 | 11/2013 | Ross et al. | |
| 9,060,810 B2 | 6/2015 | Kercher et al. | |
| 2002/0151978 A1* | 10/2002 | Zacouto ............. | A61B 17/6491 623/17.12 |
| 2009/0281542 A1* | 11/2009 | Justis ................. | A61B 17/7017 606/60 |
| 2009/0306717 A1* | 12/2009 | Kercher ............. | A61B 17/7011 606/258 |

(Continued)

FOREIGN PATENT DOCUMENTS

AU 2016200177 A1 7/2016

*Primary Examiner* — Nicholas J Plionis
*Assistant Examiner* — Steven J Cotroneo
(74) *Attorney, Agent, or Firm* — Foley & Lardner LLP

(57) ABSTRACT

A self-actuating growing rod systems for the correction of orthopedic deformities. The system comprises at least one static rod, at least one growth rod, at least one sealing component, at least one fluid reservoir, at least one injection port and at least one pressure compensating mechanism which is adapted to cause net elongation of the growth rod. The system of the present disclosure is implanted onto the bony anatomy after bringing the deformed bony anatomy to the expected position. The system of the present disclosure is then surgically implanted onto the corrected bony anatomy. As growth occurs, the system of the present disclosure distracts; thereby enabling growth and maintaining the deformity correction.

19 Claims, 10 Drawing Sheets

(56) References Cited

U.S. PATENT DOCUMENTS

2012/0130428 A1   5/2012  Hunziker
2016/0199101 A1*  7/2016  Sharifi-Mehr ..... A61B 17/7017
                                              606/258

* cited by examiner

SELF-ACTUATING GROWING ROD SYSTEMS

CROSS-REFERENCE TO RELATED PATENT APPLICATIONS

The present application takes priority from the previously filed Indian application number 201621036216 titled "Self-Actuating Hydraulic Spring based Growing Rod System" dated 24 Oct. 2016 and Indian application number 201621036220 titled "Self-Actuating Pressure Balance Chamber based Growing Rod System" dated 24 Oct. 2016.

FIELD

The present disclosure relates to self-actuating growing rod systems. Particularly, the present disclosure relates to self-actuating growing rod systems for growth induced orthopedic deformity correction.

Description of Terms

The term 'orthopedic' used herein is meant to be understood in the general sense of the word and for the purpose of the present disclosure, includes relating to the musculoskeletal system.

The term 'bony anatomy' used herein is meant to be understood in the general sense of the word and for the purpose of the present disclosure, includes all the bones and associated joints in the human skeleton.

The term 'tapering' used herein is meant to be understood in the general sense of the word and for the purpose of the present disclosure, includes one having a constant slope or a variable slope generated through steps.

The term 'distraction' used herein is meant to be understood in the general sense of the word used in the present context and for the purpose of the present disclosure includes elongation of the growing rod to accommodate the natural growth of the bony anatomy.

The term 'self-actuating' used herein is meant to be understood in the general sense of the word used in the present context and for the purpose of the present disclosure includes self-distracting to accommodate the natural growth of the bony anatomy The term 'Quasistatic distraction process' used herein is meant to be understood in the general sense of the words used in the present context and for the purpose of the present disclosure includes the process facilitated through the net elongation or distraction force generated as a result of a combination or otherwise of applied force and the natural growth of the bony anatomy and the compressive forces due to the patient's weight.

The term 'hydraulic accumulator' used herein is meant to be understood in the general sense of the term and for the purpose of the present disclosure includes a pressure storage reservoir in which a hydraulic fluid is held under the pressure exerted by a spring and a compressed gas.

The numeral '100' is used to denote the self-actuating growing rod system of the present disclosure having the three embodiments 100a, 100b and 100c.

BACKGROUND

Orthopedic deformities are the deformities involving the musculoskeletal system. Hands, legs, spine, elbows and shoulders are the commonly observed parts of the bony anatomy to be affected by deformities. A typical treatment measure for the afore-stated afflictions in younger patients or children consists of bringing the deformed bony anatomy to the expected position and implanting metal rods, also known as growing rods, thereon to maintain the desired position; thereby correcting the deformity while enabling growth of the child.

Scoliosis is a classic example of orthopedic deformity wherein the patient presents with a C- or S-shaped curve in the spine, when viewed from the posterior side. Early Onset Scoliosis (EOS) is a variant of scoliosis that is typically observed in children below 10 years of age. In EOS, the degree of curve of the deformed spine may remain constant or may change with the passage of time. Pain is typically not present, however, the condition may reduce the thoracic cavity space which severely compromises the lung growth and function resulting in fatalities including death. Further, the treatment regime includes surgically implanting growing rods along the deformed spine at the first incidence and following it up with periodic surgeries to manually distract the rod to match the growth of the patient. The periodic surgeries can be as frequent as every six months and are associated with risks such as skin infections, and pulmonary complications, besides overnight hospitalization for monitoring purposes. Even further, young children with severe spinal deformities often have multiple other medical complications resulting in an overall compromised health status and quality of life. The stress from repeated surgeries also becomes overly burdensome for the patients and their families. The currently used growing rod systems require external stimuli and apparatus for distraction. The stimulation is classified into manual stimulation, mechanical stimulation and magnetic stimulation.

Manual distraction is the procedure which requires the surgeon to reopen the original incision, reach the implanted rod and physically distract the same using his hands. This procedure is to be repeated every time depending on the extent of the growth of the patient. Rod breakage, skin infections, wound complications and the like are the various drawbacks associated with the manual distraction process.

Use of growing rods with sliding mechanism is an example of mechanical distraction. Dual metal rods are fixed posteriorly to the corrected apex of the spine with a limited number of contact points to allow vertebral growth. The technique allows growth through passive sliding of the rod through the attachment. However, the mechanical sliding action creates metal wear debris and results in tissue necrosis. Further, the implant tends to protrude from the back of the patient and causes skin infections due to the open-ended sliding rod.

Magnetic growing rods involve the use of an external magnet to distract the rod. The disadvantage of using this technology is that the rod has to be implanted closer to the skin to enable effective actuation. Being closer to the skin increases the chances of wound complications, prominent protrusions and more unplanned surgical procedures. Further, such a placement necessitates that the rod has lesser points of attachment to the spine, with a much longer length of the rod remaining unsupported. This may result in stress fractures in the rods and may also cause screw pullout. Although the magnetic system does not need invasive procedures, it needs stringent follow—up procedures. Many times, these distractions are based on the measurements done on previous patients and may lead to miscalculated distractions in some patients leading to instrumentation failure.

Growing rods working on the principle of hydraulics are also disclosed in the prior art. However, the afore-stated rods need external stimuli to cause the distraction which involves repetitive surgical interventions by surgeons that can prove to be expensive. This is notwithstanding wound complications, prominent protrusions and infection which is the risk associated with repeat surgical interventions.

In view of the severe disadvantages associated with the growing rods currently used for deformity correction, the dire need for developing growing rods which operate without any external driving force is apparent. The inventors of the present disclosure provide self-actuating growing rod systems for orthopedic deformity correction which addresses the afore-stated concerns.

OBJECTS

It is an object of the present disclosure to provide self-actuating growing rod systems.

It is another object of the present disclosure to provide self-actuating growing rod systems for orthopedic deformity correction.

It is yet another object of the present disclosure to provide self-actuating growing rod systems for orthopedic deformity correction which are safe.

It is still another object of the present disclosure to provide self-actuating growing rod systems for orthopedic deformity correction which are economical.

It is yet another object of the present disclosure to provide self-actuating growing rod systems for orthopedic deformity correction which are aesthetic.

It is still another object of the present disclosure to provide self-actuating growing rod systems for spinal deformity correction.

It is yet another object of the present disclosure to provide self-actuating growing rod systems for spinal deformity correction which mitigate or eliminate the need for repeat surgical intervention.

It is still another object of the present disclosure to provide growing rod systems for spinal deformity correction which are self-actuated and apply a continuous distraction force to enable growth and maintain correction.

SUMMARY

The present disclosure provides self-actuating growing rod systems (100) for orthopedic deformity correction, particularly, spinal deformity correction. The system of the present disclosure comprises at least one static rod (2) being in the form of a cylinder with an internal bore and comprising a first static end (2a) and a second static end (2b); wherein said first static end (2a) is tapering and is adapted to be affixed to the bony anatomy by means of at least one fixation element (4); at least one growth rod (6), coaxially coupled with said static rod (2) and comprising a first growth end (6a) and a second growth end (6b); wherein said first growth end (6a) is tapering and protrudes out of said static rod (2) and is adapted to be affixed to the bony anatomy by means of said at least one fixation element (4) and said second growth end (6b) is disposed within the cylinder bore of said static rod (2) and is adapted to function as a piston with respect to said cylinder bore and said growth rod (6) is adapted to distract longitudinally out of the cylinder bore of said static rod (2); said distraction being self-actuating, growth driven and individual dependent; at least one sealing component (8) adapted to prevent leakage of said sterile biocompatible fluid from the present system; said sealing component (8) being engageable with the second static end (2b) of said static rod (2) whilst allowing said growth rod (6) to pass there-through; thereby maintaining the position of said growth rod (6) with respect to said static rod (2) and defining the area enclosed within the inner bore of said static rod (2) as a fluid reservoir (10); at least one fluid reservoir (10) in the inner bore of said static rod (2), comprising at least one sterile biocompatible fluid; said reservoir (10) further comprising at least one trailing chamber (10a) and optionally, at least one leading chamber (10b); at least one pressure compensating mechanism (12) adapted to cause net elongation of said growth rod (6); and at least one injection port (14) adapted to facilitate injection of said sterile biocompatible fluid into said fluid reservoir (10) at a predetermined pressure. The pressure compensating mechanism (12) in one embodiment comprises at least one hydraulic spring (12a) at the second growth end (6b) of said growth rod (6) and at least one hydraulic seal (12b) located at the point of contact of said hydraulic spring (12a) and the inner bore of said static rod (2). The pressure compensating mechanism (12) in another embodiment comprises at least one fluid transfer channel (12d), at least one pressure balancing chamber (12e) and at least one hydraulic seal (12b). The pressure compensating mechanism (12) in yet another embodiment comprises a plurality of hydraulic accumulators (12f) in fluid communication with said injection port(s) (14) independently through at least one connecting element (12g), accompanied by at least one hydraulic seal (12b).

BRIEF DESCRIPTION OF THE ACCOMPANYING DRAWINGS

The present disclosure is illustrated in the accompanying non-limiting drawings, throughout which like reference letters indicate corresponding parts in the various figures.

DESCRIPTION

Figure 1:
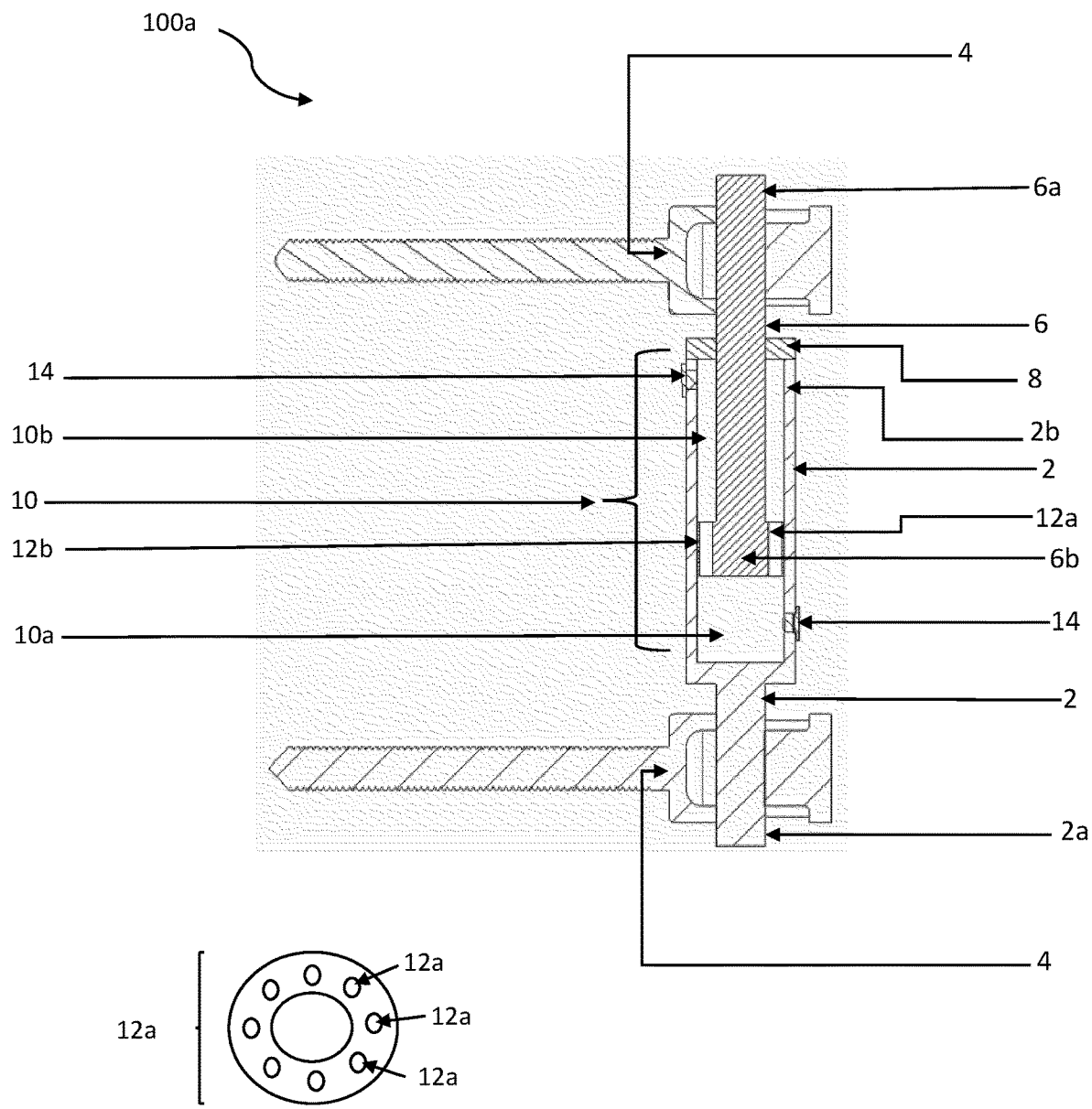
FIG. 1 illustrates a vertical cross section of one embodiment (100a) of the self-actuating growing rod system of the present disclosure (100).
Figure 2:
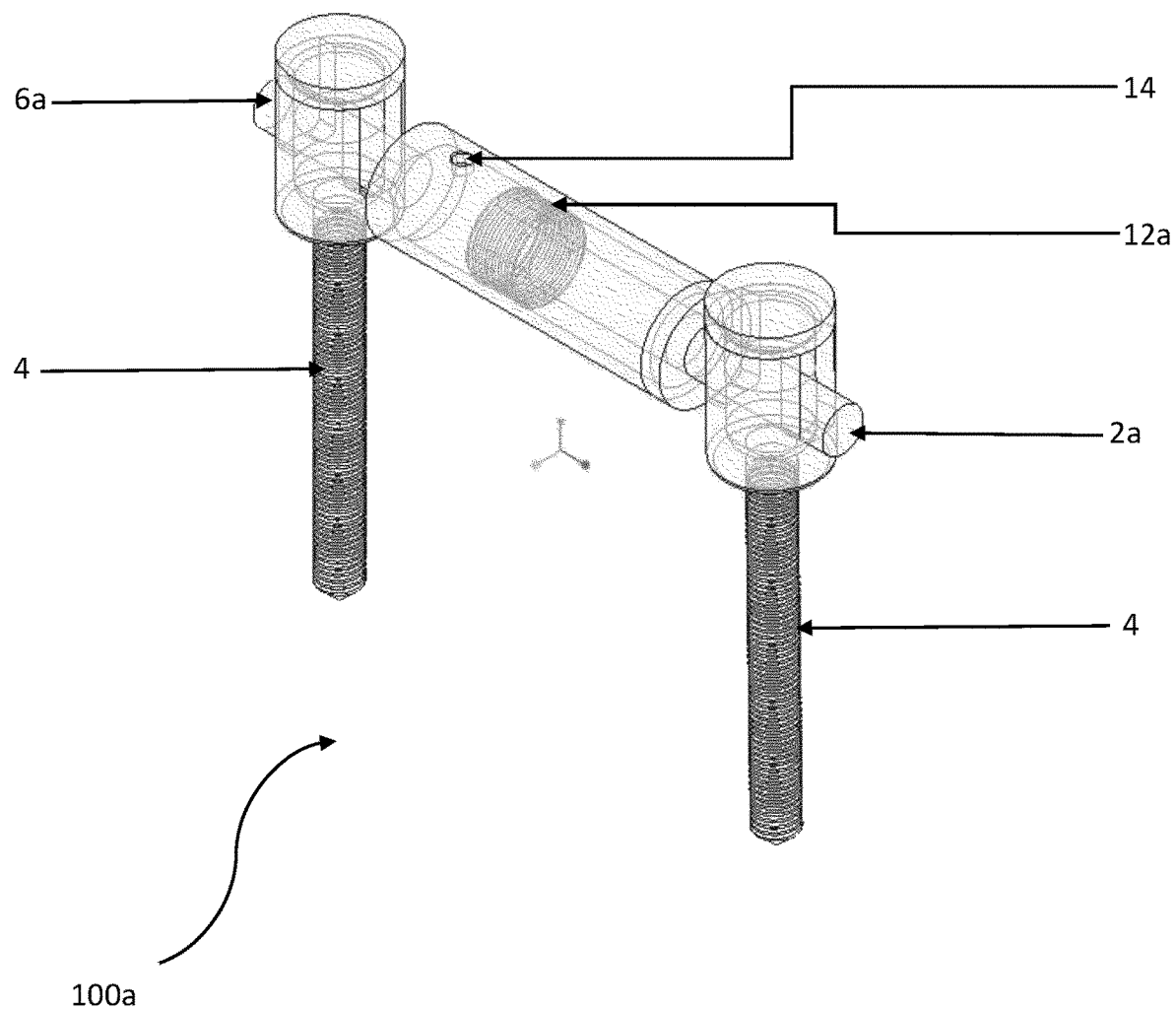
FIG. 2 illustrates a three-dimensional representation of one embodiment (100a) of the self-actuating growing rod system of the present disclosure (100).
Figure 3:
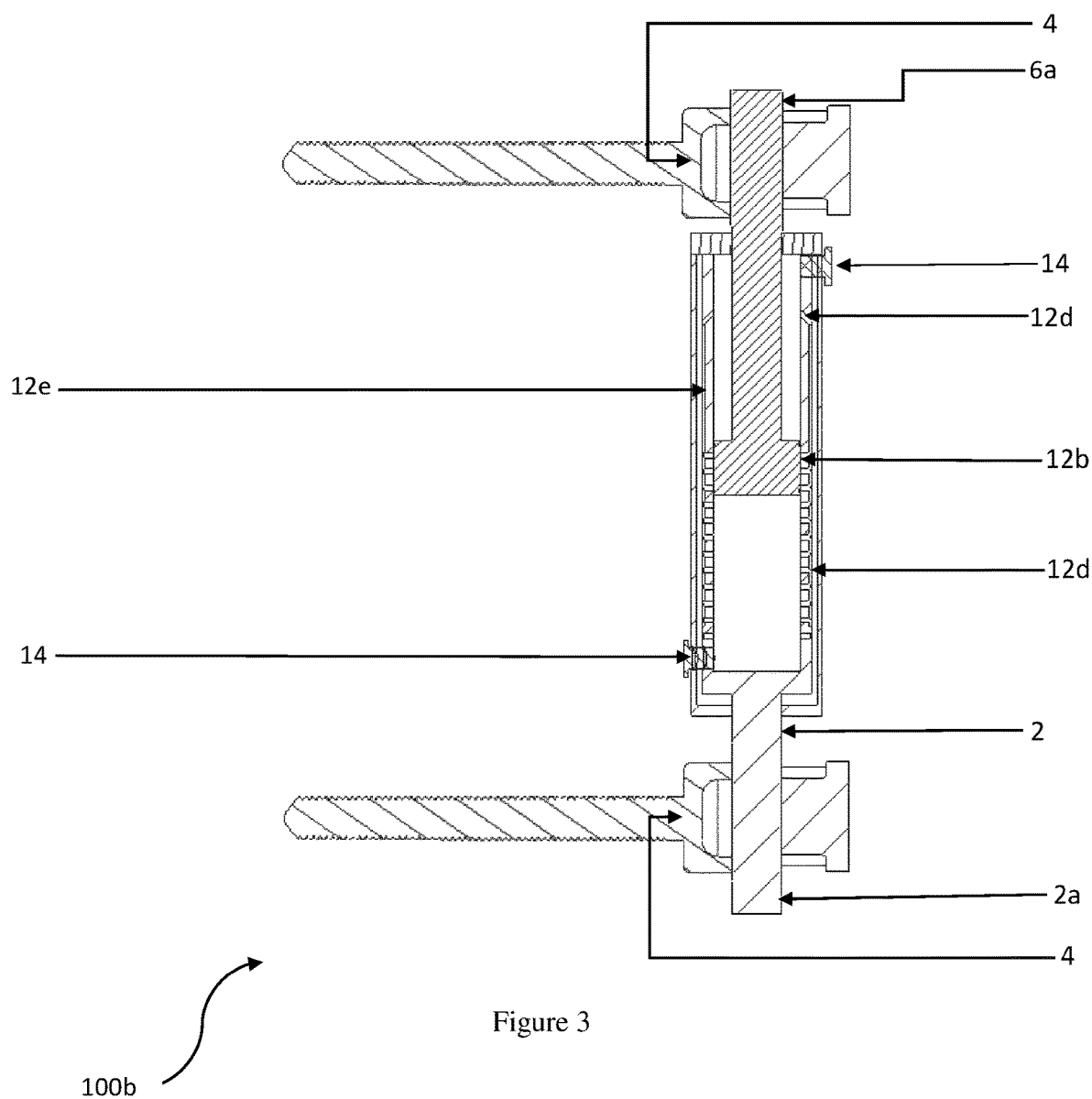
FIG. 3 illustrates a vertical cross section of another embodiment (100b) of the self-actuating growing rod system of the present disclosure (100).
Figure 4:
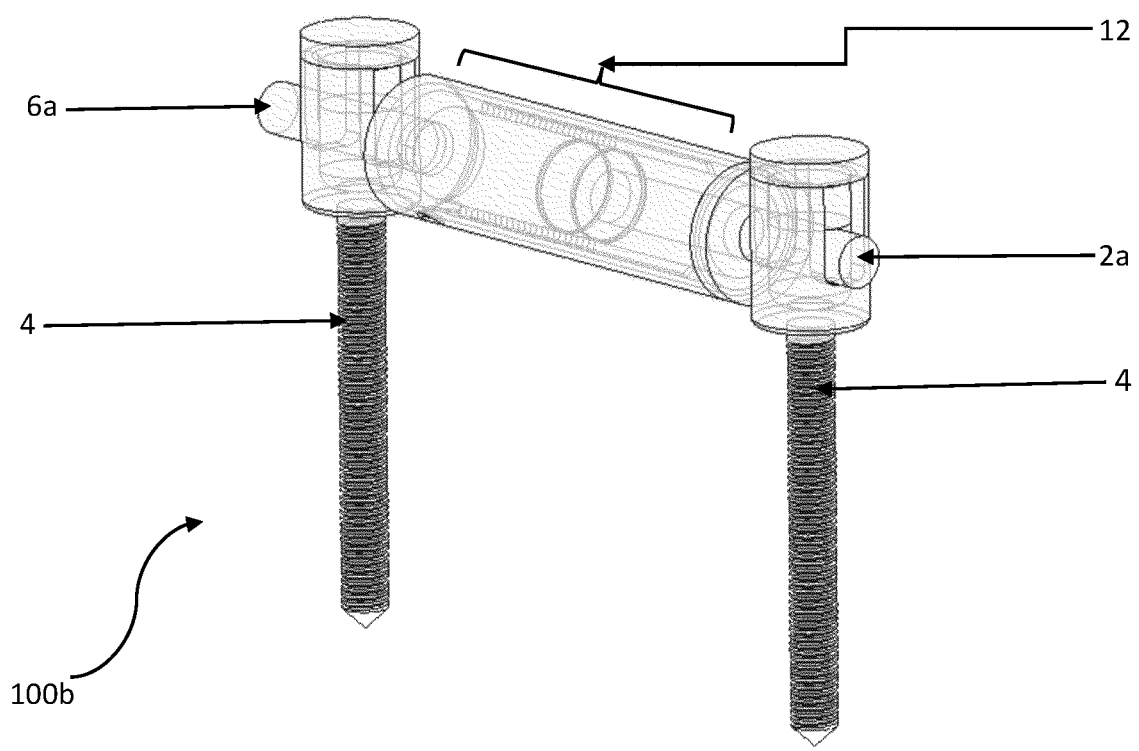
FIG. 4 illustrates a three-dimensional representation of another embodiment (100b) of the self-actuating growing rod system of the present disclosure (100).
Figure 5:
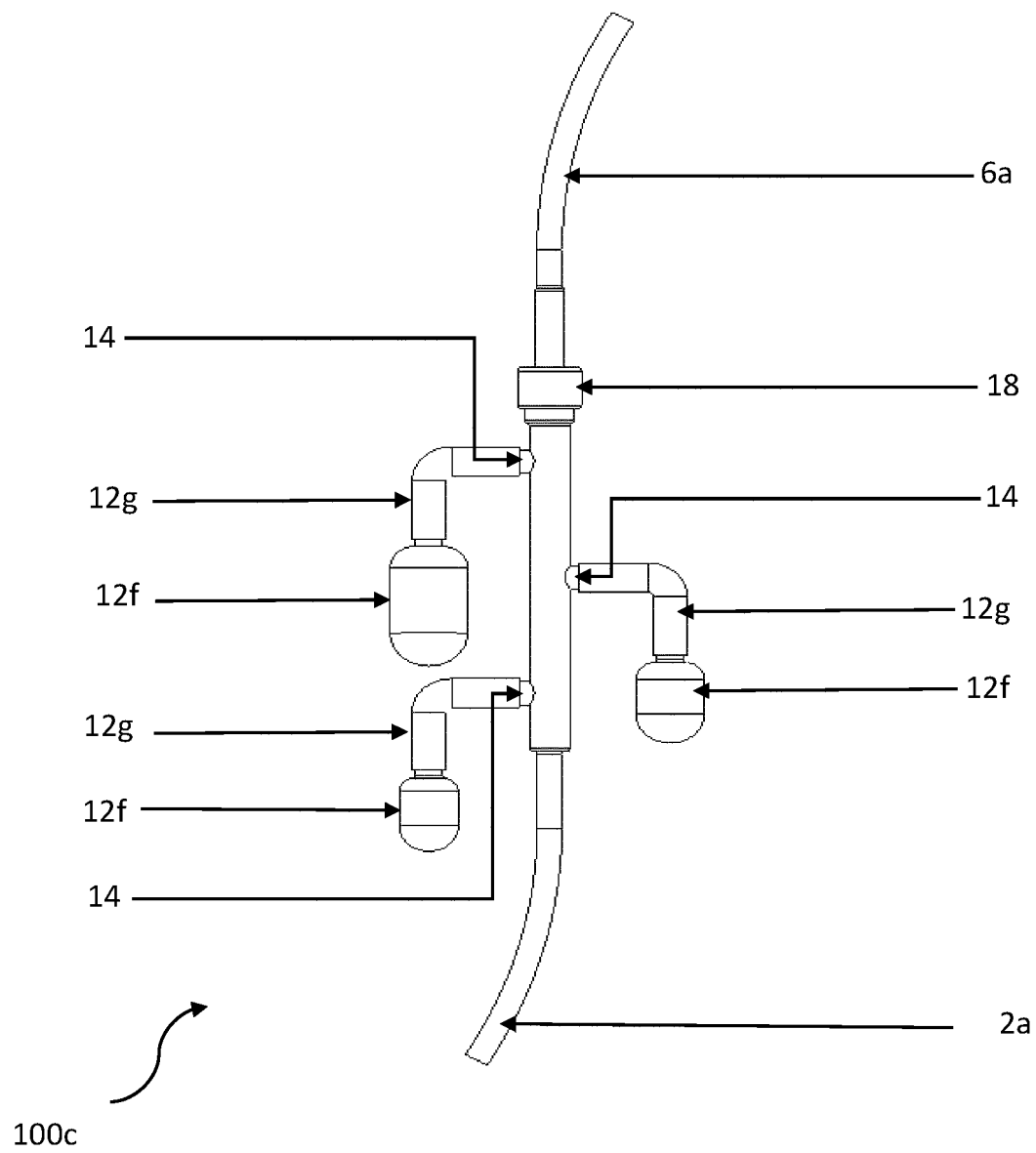
FIG. 5 illustrates a vertical cross section of a yet another embodiment (100c) of the self-actuating growing rod system of the present disclosure at the initial stage (100).
Figure 6:
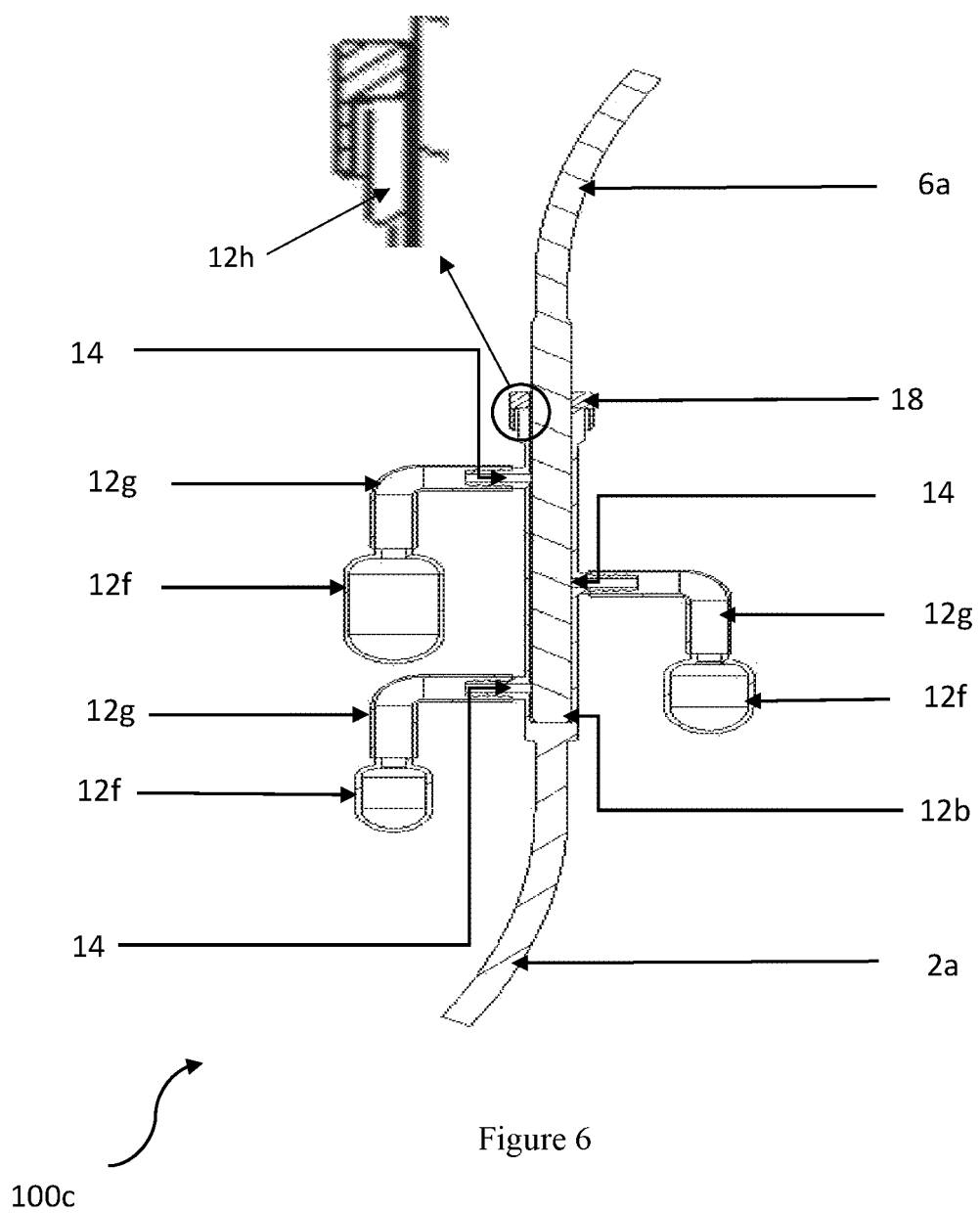
FIG. 6 illustrates an outwardly representation of a yet another embodiment (100c) of the self-actuating growing rod system of the present disclosure at the initial stage (100).
Figure 7:
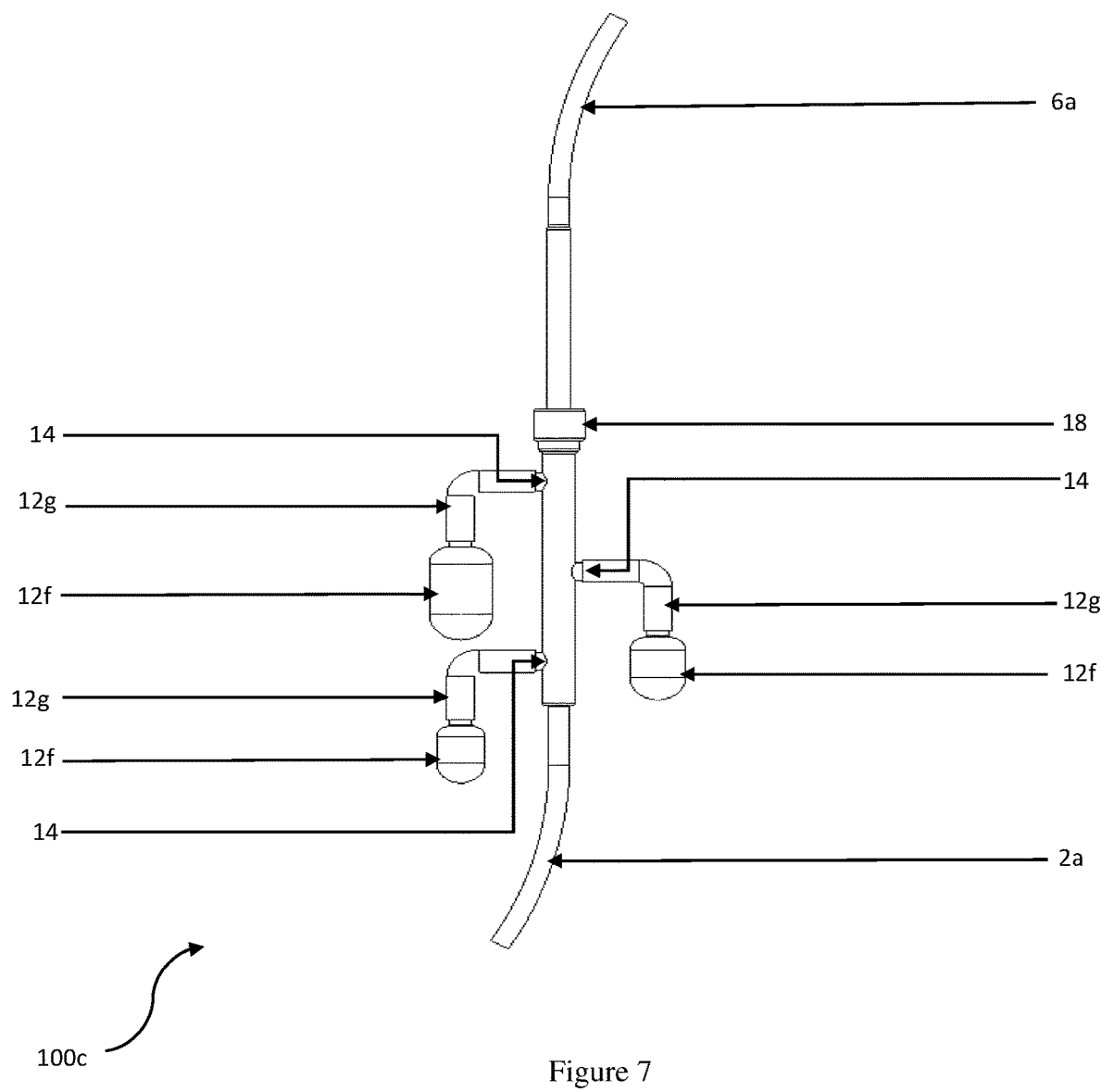
FIG. 7 illustrates a vertical cross section of the yet another embodiment (100c) of the self-actuating growing rod system of the present disclosure at a subsequent stage (100).
Figure 8:
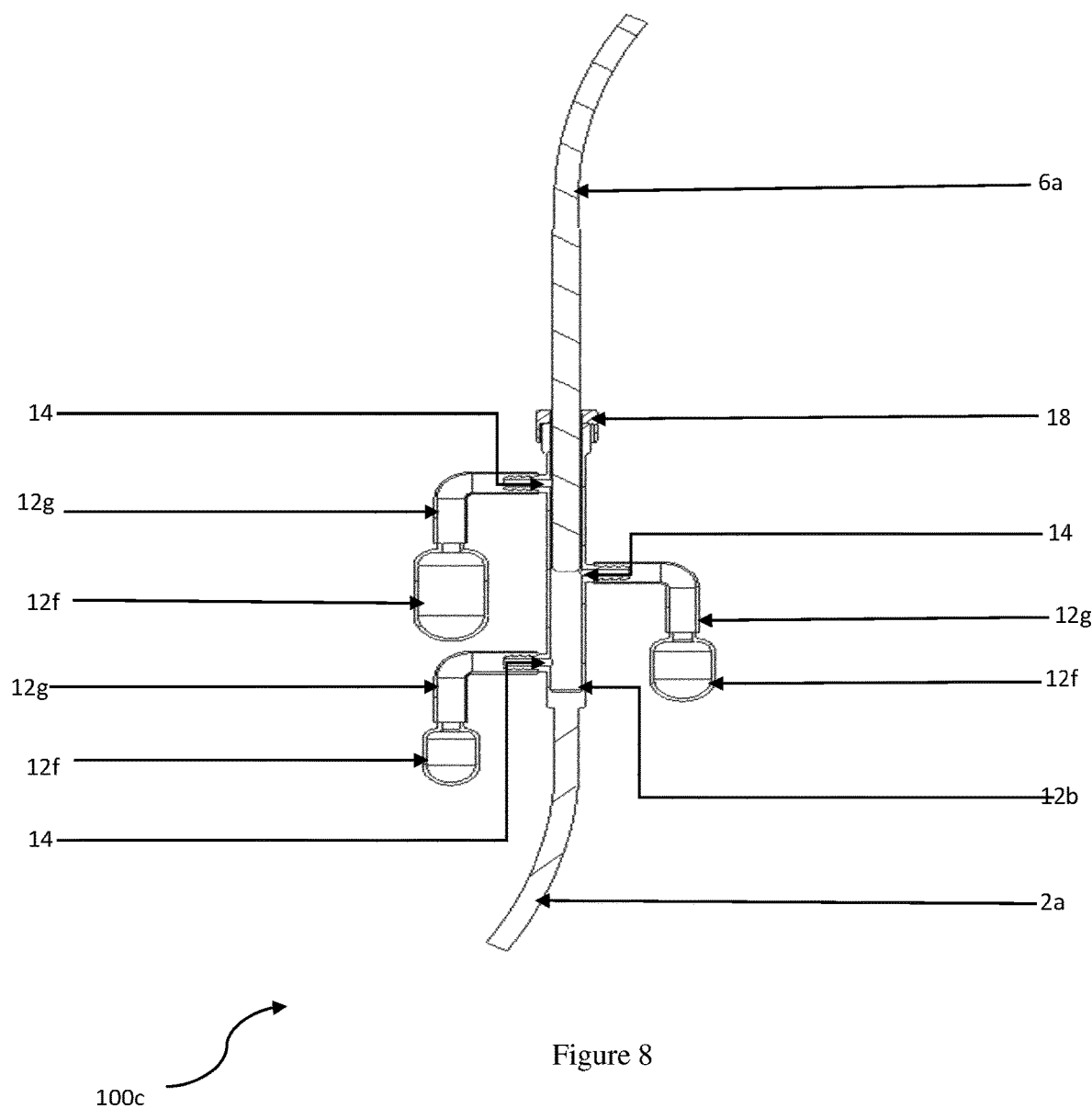
FIG. 8 illustrates an outwardly representation of the yet another embodiment (100c) of the self-actuating growing rod system of the present disclosure at a subsequent stage (100).
Figure 9:
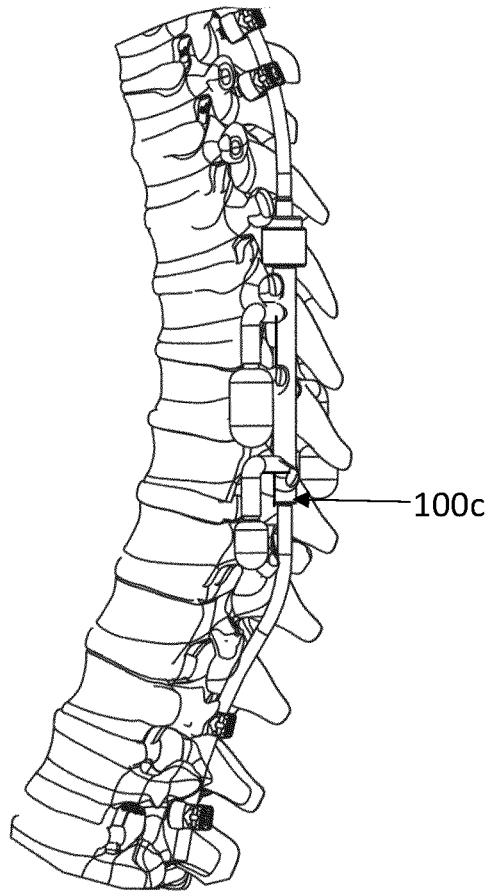
FIG. 9 illustrates the side view of the yet another embodiment (100c) of the self-actuating growing rod system of the present disclosure upon implantation on the spine (100).
Figure 10:
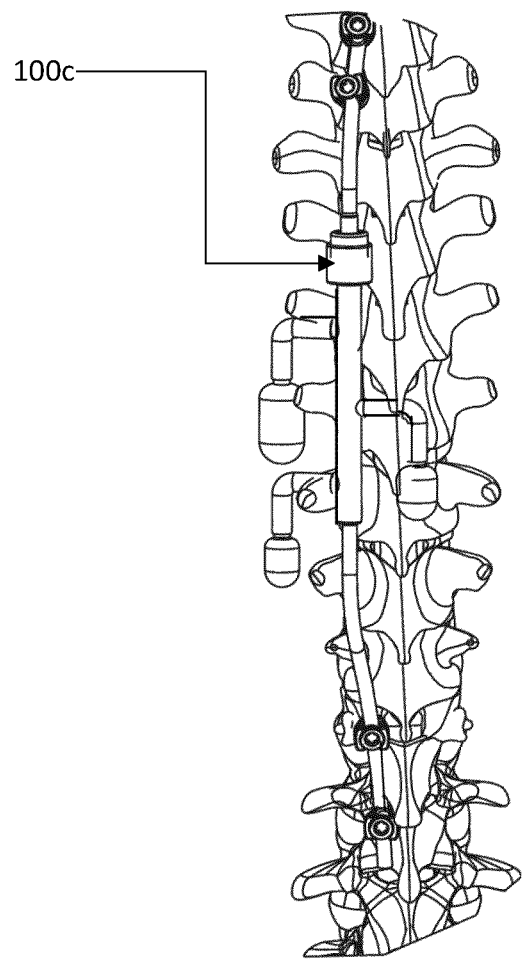
FIG. 10 illustrates the isometric view of the yet another embodiment (100c) of the self-actuating growing rod system of the present disclosure upon implantation on the spine (100).

The present disclosure, in accordance with one aspect, provides a self-actuating growing rod system (100) for orthopedic deformity correction. The system of the present disclosure works on the principle of hydraulics, however, does not require any external stimuli for distraction; thereby obviating drawbacks such as skin infections, wound complications and expensive treatment regimen. Furthermore, as the mechanism of working of the present system (100) is driven by the natural growth and constant distraction force(s) and due to the system's dependability on individuals, the incidences of collapse of the system due to the increase in patient weight and height and the associated physiological changes are minimized. In one embodiment, the growing rod system of the present disclosure is used for spinal deformity correction. The growing rod system (100) of the present disclosure comprises the components described herein below.

Before implanting the system of the present disclosure (100) onto the bony anatomy, the deformed bony anatomy is first brought to the expected position. The system of the present disclosure (100) is then surgically implanted onto the corrected bony anatomy. As growth occurs, the system of the present disclosure (100) distracts; thereby supporting the bony anatomy and correcting the deformity permanently.

The growing rod system of the present disclosure comprises at least two rods—at least one static rod (2) and at least one growth rod (6) that are to be affixed to the deformed bony anatomy at pre-determined locations. With the passage of time, as the natural growth of the patient progresses, the hydraulic mechanism of the system facilitates the distraction of the growth rod (6) so as to support the grown bony anatomy; whereas the static rod (2) remains static and attached to the previous position. This cumulatively results in maintaining the bony anatomy in the desired position; thereby correcting the deformity.

The static rod (2) of the present disclosure is hollow and assumes the form of a cylinder with an internal bore. The static rod comprises (2) a first static end (2a) and a second static end (2b). The first static end (2a) is tapering and is adapted to be affixed to the bony anatomy by means of at least one fixation element (4). In one embodiment, the first static end (2a) is affixed below the deformity site. The static rod (2) has a cross section of a shape selected from the group consisting of circular, elliptical, rectangular, toroidal, rhomboidal, irregular, cross-sectional shape made from two interlocking circles connected by flats or any other suitable cross section for the present purpose.

The static rod (2) and the growth rod (6) may have an anti-rotation feature disposed in at least one location selected from the group consisting of within the cylinder bore of the static rod (2), the second growth end (6b) of the growth rod (6), the second static end (2b) of the static rod (2) and the first growth end (6a) of the growth rod (6). The anti-rotation feature is in at least one form selected from the group consisting of gears, splines, keys, ratchet or any other suitable mechanism.

The fixation element (4) of the present disclosure is at least one selected from the group consisting of screw(s), hook(s), band(s), wire(s), connector(s), plate(s), staple(s) or any other fixation element typically used in orthopedic surgery.

The growth rod (6) of the present disclosure comprises a first growth end (6a) and a second growth end (6b). The growth rod (6) is coaxially coupled with the static rod (2) in such a way that the first growth end (6a) protrudes out of the static rod (2) and the second growth end (6b) is disposed within the cylinder bore of the static rod (2). The first growth end (6a) is tapering and adapted to be affixed to the bony anatomy by means of at least one of the afore-mentioned fixation element(s) (4). In one embodiment, the first growth end (6a) is affixed above the deformity site. The second growth end (6b) is adapted to function as a piston with respect to said cylinder bore in order to enable the growth of the bony anatomy. The growth rod (6) has a cross section of a shape selected from the group consisting of circular, elliptical, rectangular, toroidal, rhomboidal, irregular, cross-sectional shape made from two interlocking circles connected by flats or any other suitable cross section for the present purpose.

The growing rod system (100) comprises at least one sealing component (8) which is engageable with the second static end of the static rod (2b). The sealing component (8) defines the area enclosed within the inner bore of the static rod (2) as the fluid reservoir (10).

The fluid reservoir (10) is filled with at least one sterile biocompatible fluid having a pre-determined pressure. The sterile biocompatible fluid of the present disclosure is at least one selected from the group consisting of water, deionized water, saline solution or any other suitable fluid for in vivo clinical applications. The presence of the growth rod (6) divides the fluid reservoir (10) into at least one trailing chamber (10a) and optionally, at least one leading chamber (10b).

The function of the sealing component (8) is to prevent leakage of the sterile biocompatible fluid from the reservoir (10). The sealing component (8) also facilitates the passing of the growth rod (6) there-through; whilst maintaining the position of the growth rod (6) with respect to the static rod (2).

The growing rod system of the present disclosure (100) further comprises at least one injection port (14) which is adapted to facilitate injection or entry of the sterile biocompatible fluid into the fluid reservoir (10).

The growing rod system of the present disclosure (100) further comprises at least one pressure compensating mechanism (12) that is adapted to compensate the pressure differential in the system due to the natural growth of the bony anatomy and cause net elongation of the growth rod (6); thereby maintaining constant support to the corrected bony anatomy.

In one embodiment, the pressure compensating mechanism (12) comprises at least one hydraulic spring (12a) at the second growth end (6b) of the growth rod (6) accompanied by at least one hydraulic seal (12b). The hydraulic spring (12a) is formed from the second growth end (6b) of the growth rod (6) being circumferentially surrounded by at least one fluid transfer medium (12c) selected from the group consisting of porous membrane(s), valve(s) and orifice(s). The hydraulic seal (12b) is present at the point of contact of the hydraulic spring (12a) and the inner bore of the static rod (2) to prevent leakage of the sterile biocompatible fluid and maintain the pressure balance in the fluid reservoir (10). The hydraulic seal (12b) is at least one selected from the group consisting of O-ring(s), lip seal(s), quad seal(s) or any suitable seals that suit the present application.

As growth occurs with age, distraction forces are exerted on the growth rod (6) through the fixation element(s) (4).

This causes the growth rod (6) to move co-axially in the longitudinal direction resulting in a decrease in volume of the leading chamber (10b) and an increase in volume of the trailing chamber (10a). Consequently, the pressure of the sterile biocompatible fluid in the leading chamber (10b) increases and the pressure of the sterile biocompatible fluid in the trailing chamber (10a) decreases. This pressure differential in the fluid reservoir (10) is compensated by the hydraulic spring (12a) which facilitates the movement of the sterile biocompatible fluid from the leading chamber (10b) to the trailing chamber (10a). At the same time, the weight of the patient and the compressive forces of the bony anatomy exert forces opposite to the distraction force on the system of the present disclosure. However, the hydraulic spring (12a) also enables movement of the sterile biocompatible fluid in the trailing chamber (10a) to the leading chamber (10b) which not only prevents the system from collapse, but also facilitates a quasistatic distraction process which causes net elongation of the growth rod (6). Thus, the system of the present disclosure (100) being growth dependent, ensures that the bony anatomy is supported and the corrected position of the bony anatomy is maintained throughout and after the natural growth of the patient. Characteristically, the distraction of the growth rod (6) of the present disclosure is proportional to the natural growth of the bony anatomy.

For the purpose of the present embodiment, the injection port (14) is characterized as being adapted to receive the sterile biocompatible fluid ex vivo—before the implantation of the growing rod system on to the bony anatomy. This is a characterizing feature of the present system as the injection ports (14) of the growing rod systems, if mentioned, in the prior art are all adapted to receive the hydraulic fluid in vivo—on the operation table under the supervision of a medical practitioner. Devices which include but are not limited to fluid pumps, manual syringes, conventional vascular access ports or devices powered by electric motors or air compressors, may be used for injecting the sterile biocompatible fluid inside the leading (10b) and trailing chamber (10a). In one embodiment, however, the injection port (14) may receive the biocompatible fluid in vivo, in case of emergencies.

In another embodiment, the pressure compensating mechanism (12) comprises at least one fluid transfer channel (12d), at least one pressure balancing chamber (12e) and at least one hydraulic seal (12b). The fluid transfer channel (12d) connects the leading chamber (10b) to the pressure balancing chamber (12e) and the pressure balancing chamber (12e) to the trailing chamber (10a). The fluid transfer channel (12d) is at least one selected from the group consisting of porous membrane(s), valve(s) and orifice(s). The pressure balancing chamber (12e) of the present embodiment is adapted to hold the sterile biocompatible fluid rendered through the fluid transfer channel (12d) and convey the same from the leading chamber (10b) and/or to the trailing chamber (10a). The hydraulic seal (12b) is present at the point of contact of the second growth end (6b) of the growth rod (6) and the inner bore of the static rod (2) to prevent leakage of the sterile biocompatible fluid and maintain the pressure balance in the fluid reservoir (10). The hydraulic seal (12b) is at least one selected from the group consisting of O-ring(s), lip seal(s), quad seal(s) or any suitable seals that suit the present application.

As growth occurs with age, distraction forces are exerted on the growth rod (6) through the fixation element(s) (8). This causes the growth rod (6) to move co-axially in the longitudinal direction resulting in a decrease in volume of the leading chamber (10b) and an increase in volume of the trailing chamber (10a). Consequently, the pressure of the sterile biocompatible fluid in the leading chamber (10b) increases and the pressure of the sterile biocompatible fluid in the trailing chamber (10a) decreases. This pressure differential in the fluid reservoir (10) is compensated by the movement of the sterile biocompatible fluid from the leading chamber (10b) to the pressure balancing chamber (12e) and from the pressure balancing chamber (12e) to the trailing chamber (10a) via the fluid transfer channel(s) (12d). At the same time, the weight of the patient and the compressive forces of the bony anatomy exert forces opposite to the distraction force on the system of the present disclosure. However, the fluid transfer channel (12d) and the pressure balancing chamber (12e) enables movement of the sterile biocompatible fluid from the trailing chamber (10a) to the leading chamber (10b) which not only prevents the system from collapse, but also facilitates a quasistatic distraction process which causes net elongation of the growth rod (6). Thus, the system of the present disclosure being growth dependent, ensures that the bony anatomy is supported and the corrected position of the bony anatomy is maintained throughout and after the natural growth of the patient. Characteristically, the distraction of the growth rod of the present disclosure is proportional to the natural growth of the bony anatomy.

For the purpose of the present embodiment, the injection port (14) is characterized as being adapted to receive the sterile biocompatible fluid ex vivo—before the implantation of the growing rod system on to the bony anatomy. This is a characterizing feature of the present system as the injection ports (14) of the growing rod systems, if mentioned, in the prior art are all adapted to receive the hydraulic fluid in vivo—on the operation table under the supervision of a medical practitioner. Devices which include but are not limited to fluid pumps, manual syringes, conventional vascular access ports or devices powered by electric motors or air compressors, may be used for injecting the sterile biocompatible fluid inside the leading (10b) and trailing chamber (10a). In one embodiment, however, the injection port (14) may receive the biocompatible fluid in vivo, in case of emergencies.

In yet another embodiment, the pressure compensating mechanism (12) comprises a plurality of hydraulic accumulators (12f) in fluid communication with at least one of the injection port (14) independently through at least one connecting element (12g), accompanied by at least one hydraulic seal (12b). For the purpose of the present embodiment, the growing rod almost entirely covers the internal bore of the static rod (2) and consequently, there is no leading chamber (10b). However, in one embodiment, the growing rod (6) does not completely cover the internal bore of the static rod (2) resulting in a leading chamber (10b) and a trailing chamber (10a). The accumulator (12f) of the present embodiment contains the sterile biocompatible fluid at a pre-determined pressure to apply constant distraction force and compensate for the volume created due to the distraction of the growth rod (6). The accumulator (12f) used in the present embodiment is of at least one type selected from the group consisting of bladder based accumulator and spring based accumulator.

As growth occurs with age, distraction forces are exerted on the growth rod through the fixation element(s) (8). This causes the growth rod (6) to move co-axially in the longitudinal direction which gradually uncovers the injection port (14) connecting the fluid reservoir (10) to the accumulator (12f). The uncovering of the injection port (14) causes the sterile biocompatible fluid contained in the accumulator (12f) to enter into the trailing chamber (10a). As the patient grows and the growth rod distracts further, the injection ports (14) open progressively and the sterile biocompatible fluid contained therein enters the trailing chamber (10a).

It is significant to note that, the weight of the patient and the compressive forces of the bony anatomy exert forces opposite to the distraction force on the system of the present disclosure (100). This may cause the present system to collapse. The accumulators of the present embodiment are designed to avoid such a collapse. The pressure compensating mechanism (12) of the present embodiment maintains a constant distraction force to balance the compressive force acting on the system which not only prevents the system from collapse, but also facilitates a quasistatic distraction process which causes net elongation of the growth rod (6). Thus, the system of the present disclosure being growth dependent, ensures that the bony anatomy is supported and the corrected position of the bony anatomy is maintained throughout and after the natural growth of the patient. Characteristically, the distraction of the growth rod (6) of the present disclosure is proportional to the natural growth of the bony anatomy.

Figure 11:
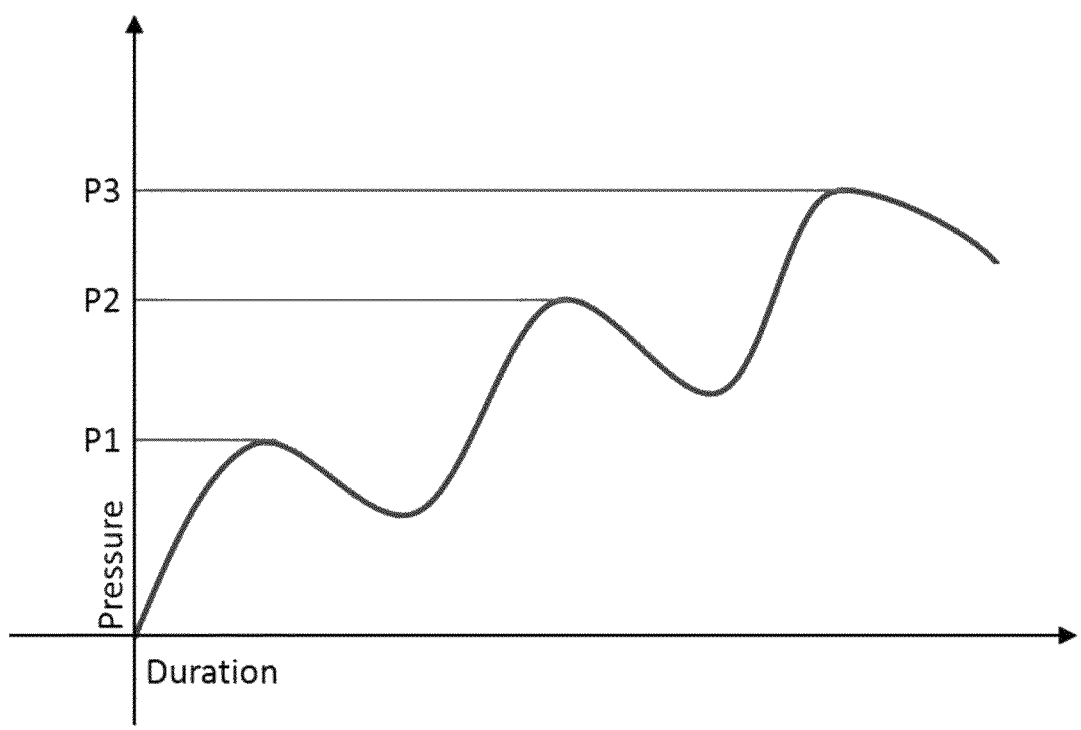
FIG. 11 is a graphic demonstration of the working of the pressure compensating mechanism of the yet another embodiment (100c) of the self-actuating growing rod system of the present disclosure (100).

Furthermore, in accordance with the present embodiment, the pressure compensating mechanism (12) causes net elongation of the growth rod (6) to occur in a plurality of phases. In the first phase, as a virtue of the first growth end (6a) of the growth rod (6) being affixed to the bony anatomy, in the process of the natural growth of the latter, the first growth end (6a) of the growth rod (6) gets distracted which uncovers the bottom-most injection port (14). This action generates a gradual, but stepped distraction force which in turn is balanced by the correction resistive forces and the patients' weight. In the subsequent phase(s), net elongation of the growth rod (6) is driven by the net cumulative effect of the accumulator pressure distraction force and natural growth of the bony anatomy, opposed by the correction resistive forces and patients' weight. This results in a quasistatic distraction process. The afore-stated mechanism of net elongation using the present embodiment is represented in FIG. 11.

In one embodiment, the pressure compensating mechanism (12) comprises three accumulators (12f) arranged in ascending order of pressure ratings, starting from the first static end (2a) of the static rod (2) to the second static end (2b) of the static rod (2). The pressure ratings of the accumulators are determined on the basis of the distraction force required to hold the corrective forces on the bony anatomy and support the weight of the patient through the patient's individual growth progression and cause net elongation of the growth rod (6).

The present embodiment has been designed to take into consideration the anthropometric data for patients in the prescribed age group. As growth occurs, the accumulators provide step—wise increase in the distraction force available to support the increasing weight of the patient. The same is achieved by providing multiple accumulators (12f) with increasing pressure ratings, along the length of the static rod (2) which activate gradually as the height of the patient increases. The pressure ratings are calculated based on the anthropometric data—weight available for the particular corresponding height at which it is activated. Further, the static rod (2) and the growth rod (6) are designed in a way that the rods are able to sustain the pressure exerted by the sterile biocompatible fluid. Each accumulator (12f) has a pre-determined pressure level which is maintained throughout the cycle.

The injection port(s) (14) of the present embodiment is adapted to release the sterile biocompatible fluid having a pre-determined pressure from the accumulator (12f) into the trailing chamber (10a) due to the net elongation and maintain the bony anatomy in the corrected position, preventing collapse. Characteristically, the injection port (14) has a cross section of a shape selected from the group consisting of circular, elliptical, triangular and trapezoidal. In one embodiment, the cross section is triangular which facilitates gradual release of the fluid in the trailing chamber (10a). The injection port (14) optionally comprises at least one fluid transfer medium (12c), selected from the group consisting of porous membrane(s), valve(s) and orifice(s), adapted to facilitate gradual flow of sterile biocompatible fluid at pre-determined pressure from the accumulator (12f) into the trailing chamber (10a). The hydraulic seal (12b) is located at the point of contact of the second growth end (6b) of said growth rod (6) and the inner bore of said static rod (2) and adapted to prevent leakage of said fluid and maintain pressure balance in said fluid reservoir (10). The hydraulic seal (12b) is at least one selected from the group consisting of O-ring(s), lip seal(s), quad seal(s) or any suitable seals that suit the present application.

The number of accumulators, the size of the accumulators, the sequence of attachment of the accumulators along the length of the static rod (2) and the pressure differential to be maintained therein is characterized on the basis of the distraction force required to hold the corrective forces on the bony anatomy and support the weight of the patient through the patient's individual growth progression and cause net elongation. The connecting element used for connecting the accumulator(s) (12f) with the injection port(s) (14) is flexible tubing. The connecting element (12g) has the property to be bent to fit the human anatomy. The connecting element (12g) can be fit either by virtue of geometrical tolerances or extra constraints to make the system leak proof.

For the purpose of the present embodiment, the sealing component (18) is a locking cap. The locking cap and the static rod (2) have grooves to accommodate the hydraulic seals (12b). The seal (12b) ensures that the fluid does not flow over the static rod (2). A wiper (12h) may be added to the system to scrape away fluid on the first growth end (6a) of the growth rod (6) near the second static end (2b) of the static rod (2).

The afore-stated components of the system of the present disclosure are manufactured from biocompatible materials. Further, the components of the system of the present disclosure are manufactured from at least one material selected from the group consisting of metal(s), metal alloys and polymers. For the purpose of the present disclosure, the term metal is at least one selected from the group consisting of titanium, cobalt, chromium, and stainless steel or any other metal or metal alloy suitable from biocompatibility and strength perspective. For the purpose of the present disclosure, the term polymers is at least one selected from the group consisting of high density polyethylene (HDPE), polyurethane, polycarbonate urethane, ultra-high molecular weight polyethylene (UHMWPE), polyethylene terephthalate (PET), polyether ether ketone (PEEK) and silicone or any other polymer suitable from biocompatibility and strength perspective. Further, the static rod (2) and the growth rod (6) are manufactured from a material having a shear modulus which permits slight cyclic deflections without failure. Furthermore, the static rod (2) and the growth rod (6) are manufactured from a material having ductility sufficient to permit the rods to be deformed into a curve to conform to the natural curve of the bony anatomy and to withstand the operating pressure. All the components of the growing rod system of the present disclosure may be fabricated separately and attached together using conventional manufacturing techniques. The dimensions of the growing rod system may vary depending on factors such as age, weight, height, sex and the extent of deformity.

The system of the present disclosure (100) is adapted to be implanted sub-muscularly. In one embodiment, the system of the present disclosure is adapted to be implanted sub-cutaneously as desired by the surgeon. Further, the system of the present disclosure may be adapted to attached to another instrument before being affixed to the bony anatomy.

There are numerous advantages of the system of the present disclosure. As the movement of the growth rod (6) is operated by a hydraulic mechanism there is no need of repetitive surgical treatment for adjustment of the rod with the growing bony anatomy. As the distractions happen only on the basis of the growth of the patient, the distractions are auto-regulated. As the present system has a piston-cylinder arrangement, the fluid inside the cylinder forms a thin layer in the gap between the static rod (2) and the growth rod (6) which reduces the friction and consequently the wear debris. Further, growth-guided and individual-dependent distraction of the present system makes the invasive manual distraction unnecessary which reduces the overall costs associated with repeat surgical procedures. Still further, as the present mechanism involves multiple chambers that allow transmission of fluid therethrough; spinal growth induced actuation of the rod is enabled without the need of any external driving force.

The embodiments described herein above are non-limiting. The foregoing descriptive matter is to be interpreted merely as an illustration of the concept of the present disclosure and it is in no way to be construed as a limitation. Description of terminologies, concepts and processes known to persons acquainted with technology has been avoided for the sake of brevity.

Technical Advantages and Economic Significance

The technical advantages and economic significance of the growing rod system of the present disclosure (100) are presented herein after:

the present system facilitates self-actuation;
growth guided and individual dependent distraction makes the requirement of manual distraction unnecessary;
reduced incidences of skin infections and wound complications;
reduced incidences of the system collapse due to growth of the patient;
reduced creation of metal wear debris;
being adapted for sub-muscular implantation, the system does not protrude out of the back; hence the system does not cause discomfort to the patient and may have improved aesthetics;
the system is more economical as no follow up visits for distraction of the rod are essential;
the system does not hamper growth of the patient;
the present system provides multiple point anchoring to the bony anatomy;
improvement in quality of life of the patient due to non-repetitive surgical distraction;
reduced incidences of tissue necrosis due to reduced wear debris; and
reduces chances of rod breakage as the present system is capable of being anchored at multiple points to the bony anatomy.

What is claimed is:

1. A self-actuating growing rod system comprising:
   a. at least one static rod being in the form of a cylinder with an internal bore and comprising a first static end and a second static end, wherein said first static end is tapering and is adapted to be affixed to a bony anatomy;
   b. at least one growth rod, coaxially coupled with said at least one static rod and comprising a first growth end and a second growth end; wherein said first growth end is tapering and protrudes out of said at least one static rod and is adapted to be affixed to the bony anatomy and said second growth end is disposed within the cylinder bore of said at least one static rod and is adapted to function as a piston with respect to said cylinder bore and said at least one growth rod is adapted to distract longitudinally out of the cylinder bore of said at least one static rod, said distraction being self-actuating, growth driven and individual dependent;
   c. at least one locking cap adapted to prevent leakage of at least one sterile biocompatible fluid from the self-actuating growing rod system; said at least one locking cap being engageable with the second static end of said at least one static rod whilst allowing said at least one growth rod to pass there-through, thereby maintaining the position of said at least one growth rod with respect to said at least one static rod and defining an area enclosed within an inner bore of said at least one static rod as a fluid reservoir and said at least one sterile biocompatible fluid being at least one selected from the group consisting of water, deionized water and saline solution;
   d. at least one fluid reservoir in the inner bore of said at least one static rod, comprising said at least one sterile biocompatible fluid; said reservoir further comprising at least one trailing chamber;
   e. at least one pressure compensating mechanism comprising at least one hydraulic accumulator, the at least one pressure compensating mechanism being adapted to cause net elongation of said at least one growth rod; and
   f. at least one injection port adapted to facilitate injection of said at least one sterile biocompatible fluid into said fluid reservoir at a pre-determined pressure.

2. The system as claimed in claim 1, wherein said at least one static rod is affixed to at least one rod fixated to the bony anatomy, inferior to said growing rod system and is not directly affixed to an anatomical structure.

3. The system as claimed in claim 1, further comprises a wiper to scrape away fluid on the first growth end of the at least one growth rod near the second static end of the at least one static rod.

4. The system as claimed in claim 1, wherein
   said first static end and said first growth end are adapted to be affixed to the bony anatomy using at least one fixation element; said at least one fixation element being at least one selected from the group consisting of screws, hooks, bands, wires, connectors, plates, and staples.

5. The system as claimed in claim 1, wherein components 'a' to 'f' are manufactured from biocompatible materials.

6. The system as claimed in claim 1, wherein said at least one static rod and said at least one growth rod have a cross section of a shape selected from the group consisting of circular, elliptical, rectangular, toroidal, rhomboidal, irregular, cross-sectional shapes such as two interlocking circles connected by flats or any other suitable cross section.

7. The system as claimed in claim 1, being adapted to be implanted by at least one route of implantation selected from the group consisting of sub-muscularly and subcutaneously.

8. The system as claimed in claim 1, wherein said injection port is adapted to receive said at least one sterile biocompatible fluid ex vivo, before the implantation of said growing rod system on to the bony anatomy.

9. The system as claimed in claim 1, being adapted for the correction of orthopedic deformity.

10. The system as claimed in claim 1, being adapted for the correction of spinal deformity.

11. The system as claimed in claim 1, wherein said at least one pressure compensating mechanism comprises:
a plurality of hydraulic accumulators in fluid communication with said at least one injection port independently through at least one connecting element, accompanied by at least one hydraulic seal,
wherein said at least one pressure compensating mechanism is adapted to facilitate net elongation of said at least one growth rod to occur in a plurality of phases wherein, in a first phase, a gradual, yet stepped distraction force is applied by opening of a high pressure accumulator injection port, the distraction force in turn being balanced by correction resistive forces and patients' weight, and in a subsequent phase, said net elongation is driven by the net cumulative effect of accumulator pressure distraction force and natural growth of the bony anatomy opposed by the correction resistive forces and patients' weight, thereby resulting in a quasistatic distraction process,
wherein said at least one connecting element is a flexible tubing and is adapted to be bent to fit a human anatomy,
wherein said at least one injection port having a cross section of a shape selected from the group consisting of circular, elliptical, triangular and trapezoidal is adapted to
release said at least one sterile biocompatible fluid contained in the hydraulic accumulators at a pre-determined pressure, into the trailing chamber due to said net elongation and
maintain the bony anatomy in the corrected position and preventing collapse.

12. The system as claimed in claim 11, wherein the number of the hydraulic accumulators, the size of the hydraulic accumulators, the sequence of attachment of the hydraulic accumulators along the length of said at least one static rod and the pressure differential to be maintained therein is determined on the basis of the distraction force required to hold the corrective forces on the bony anatomy and support the weight of the patient through the patient's individual growth progression and cause net elongation.

13. The system as claimed in claim 11, wherein said hydraulic accumulator is of at least one type selected from the group consisting of bladder based accumulator and spring based accumulator.

14. The system as claimed in claim 11, wherein said at least one pressure compensating mechanism comprises three accumulators arranged in ascending order of pressure ratings, starting from the first static end of said at least one static rod to the second static end of said at least one static rod.

15. A self-actuating growing rod system comprising:
at least one static rod being in the form of a cylinder with an internal bore and comprising a first static end and a second static end, wherein said first static end is tapering and is adapted to be affixed to a bony anatomy;
at least one growth rod, coaxially coupled with said at least one static rod and comprising a first growth end and a second growth end; wherein said first growth end is tapering and protrudes out of said at least one static rod and is adapted to be affixed to the bony anatomy and said second growth end is disposed within the cylinder bore of said at least one static rod and is adapted to function as a piston with respect to said cylinder bore and said at least one growth rod is adapted to distract longitudinally out of the cylinder bore of said at least one static rod, said distraction being self-actuating, growth driven and individual dependent;
at least one locking cap adapted to prevent leakage of at least one sterile biocompatible fluid from the self-actuating growing rod system; said at least one locking cap being engageable with the second static end of said at least one static rod whilst allowing said at least one growth rod to pass there-through; thereby maintaining the position of said at least one growth rod with respect to said at least one static rod and defining an area enclosed within an inner bore of said at least one static rod as a fluid reservoir and said at least one sterile biocompatible fluid being at least one selected from the group consisting of water, deionized water and saline solution;
at least one fluid reservoir in the inner bore of said at least one static rod, comprising said at least one sterile biocompatible fluid; said reservoir further comprising at least one trailing chamber;
at least one pressure compensating mechanism adapted to cause net elongation of said at least one growth rod; and
at least one injection port adapted to facilitate injection of said at least one sterile biocompatible fluid into said fluid reservoir at a pre-determined pressure,
wherein said at least one pressure compensating mechanism comprises a plurality of hydraulic accumulators in fluid communication with said at least one injection port independently through at least one connecting element, accompanied by at least one hydraulic seal,
wherein said at least one pressure compensating mechanism is adapted to facilitate net elongation of said at least one growth rod to occur in a plurality of phases wherein, in a first phase, a gradual, yet stepped distraction force is applied by opening of a high pressure accumulator injection port, the distraction force in turn being balanced by correction resistive forces and patients' weight, and in a subsequent phase, said net elongation is driven by the net cumulative effect of accumulator pressure distraction force and natural growth of the bony anatomy opposed by the correction resistive forces and patients' weight, thereby resulting in a quasistatic distraction process,
wherein said at least one connecting element is a flexible tubing and is adapted to be bent to fit a human anatomy,
wherein said at least one injection port having a cross section of a shape selected from the group consisting of circular, elliptical, triangular and trapezoidal is adapted to
release said at least one sterile biocompatible fluid contained in the hydraulic accumulators at a pre-determined pressure, into the trailing chamber due to said net elongation and
maintain the bony anatomy in the corrected position and preventing collapse,
wherein the number of the hydraulic accumulators, the size of the hydraulic accumulators, the sequence of attachment of the hydraulic accumulators along the length of said at least one static rod and the pressure differential to be maintained therein is determined on the basis of the distraction force required to hold the corrective forces on the bony anatomy and support the weight of the patient through the patient's individual growth progression and cause net elongation, and wherein said hydraulic seal being selected from the group consisting of O-rings, lip seals, and quad seals, located at the point of contact of the second growth end of said at least one growth rod and the inner bore of said at least one static rod and adapted to prevent leakage of said fluid and maintain pressure balance in said fluid reservoir and said hydraulic accumulator is of at least one type selected from the group consisting of bladder based accumulator and spring based accumulator.

16. The system as claimed in claim 15, wherein said at least one pressure compensating mechanism comprises three accumulators arranged in ascending order of pressure ratings, starting from the first static end of the at least one static rod to the second static end of the at least one static rod; said pressure ratings being determined on the basis of the distraction force required to hold the corrective forces on the bony anatomy and support the weight of the patient through the patient's individual growth progression and cause net elongation of the at least one growth rod.

17. A self-actuating growing rod system comprising:
at least one static rod being in the form of a cylinder with an internal bore and comprising a first static end and a second static end, wherein said first static end is tapering and is adapted to be affixed to a bony anatomy by means of at least one fixation element;

at least one growth rod, coaxially coupled with said at least one static rod and comprising a first growth end and a second growth end; wherein said first growth end is tapering and protrudes out of said at least one static rod and is adapted to be affixed to the bony anatomy by means of said at least one fixation element and said second growth end is disposed within the cylinder bore of said at least one static rod and is adapted to function as a piston with respect to said cylinder bore and said at least one growth rod is adapted to distract longitudinally out of the cylinder bore of said at least one static rod, said distraction being self-actuating, growth driven and individual dependent;

at least one locking cap adapted to prevent leakage of at least one sterile biocompatible fluid from the self-actuating growing rod system; said at least one locking cap being engageable with the second static end of said at least one static rod whilst allowing said at least one growth rod to pass there-through, thereby maintaining the position of said at least one growth rod with respect to said at least one static rod and defining the area enclosed within an inner bore of said at least one static rod as a fluid reservoir and said at least one sterile biocompatible fluid being at least one selected from the group consisting of water, deionized water and saline solution;

at least one fluid reservoir in the inner bore of said at least one static rod, comprising said at least one sterile biocompatible fluid;

at least one pressure compensating mechanism comprising at least one of a hydraulic accumulator, a hydraulic spring, or a fluid transfer channel, the at least one pressure compensating mechanism being adapted to cause net elongation of said at least one growth rod; and at least one injection port adapted to facilitate injection of said at least one sterile biocompatible fluid into said fluid reservoir at a pre-determined pressure.

18. The system as claimed in claim 17, wherein said at least one pressure compensating mechanism comprises at least one hydraulic spring at the second growth end of said at least one growth rod and at least one hydraulic seal located at the point of contact of said hydraulic spring and the inner bore of said at least one static rod; said hydraulic spring being formed from the second growth end of said at least one growth rod being adapted to compensate the pressure differential generated between the fluid present in at least one leading chamber and the fluid present in at least one trailing chamber both created within the fluid reservoir; thereby facilitating a quasistatic distraction process leading to net elongation of said at least one growth rod and said hydraulic seal being selected from the group consisting of O-rings, lip seals, and quad seals and being adapted to prevent leakage of said fluid and maintain pressure balance in said fluid reservoir.

19. The system as claimed in claim 17, wherein said at least one pressure compensating mechanism comprises at least one fluid transfer channel, at least one pressure balancing chamber and at least one hydraulic seal; wherein said fluid transfer channel is at least one selected from the group consisting of porous membranes, valves and orifices and is adapted to convey said at least one sterile biocompatible fluid within said fluid reservoir and compensate the pressure differential generated in at least one leading chamber and at least one trailing chamber created in said fluid reservoir; thereby facilitating a quasistatic distraction process leading to net elongation of said at least one growth rod; and said pressure balancing chamber is adapted to hold and convey said at least one sterile biocompatible fluid rendered through said fluid transfer channel to said leading chamber and/or to said trailing chamber; said hydraulic seal being selected from the group consisting of O-rings, lip seals, and quad seals and located at the point of contact of the second growth end of said at least one growth rod and the inner bore of said at least one static rod and adapted to prevent leakage of said fluid and maintain pressure balance in said fluid reservoir.

* * * * *